United States Patent [19]
Phillips

[11] Patent Number: 4,937,248
[45] Date of Patent: Jun. 26, 1990

[54] 6-PIPERIDYL CARBOSTYRIL COMPOUNDS AND COMPOSITIONS CONTAINING THEM

[75] Inventor: Arthur P. Phillips, Raleigh, N.C.

[73] Assignee: Burroughs Wellcome Co., Research Triangle Park, N.C.

[21] Appl. No.: 135,654

[22] Filed: Dec. 21, 1987

[30] Foreign Application Priority Data

Dec. 23, 1986 [GB] United Kingdom ................. 8630702

[51] Int. Cl.$^5$ ................... C07D 401/04; A61K 31/47
[52] U.S. Cl. ...................................... 514/312; 546/157
[58] Field of Search ................. 546/157, 158; 514/312

[56] References Cited

U.S. PATENT DOCUMENTS

| | | | |
|---|---|---|---|
| 2,616,855 | 11/1952 | Wheelock . | |
| 4,728,653 | 3/1988 | Campbell et al. | 546/157 |
| 4,329,347 | 5/1982 | Müller et al. | 424/251 |
| 4,415,572 | 11/1983 | Tominaga et al. | 546/157 |
| 4,710,507 | 12/1987 | Campbell et al. | 514/312 |
| 4,728,653 | 3/1988 | Campbell et al. | 514/312 |
| 4,740,513 | 4/1988 | Campbell et al. | 514/312 |

FOREIGN PATENT DOCUMENTS

| | | | |
|---|---|---|---|
| 0148623 | 7/1985 | European Pat. Off. | 546/157 |
| 0187322 | 7/1986 | European Pat. Off. . | |
| 0202760 | 11/1986 | European Pat. Off. . | |
| 0236140 | 9/1987 | European Pat. Off. . | |
| 0255134 | 2/1988 | European Pat. Off. . | |
| 2580646 | 10/1986 | France . | |
| 0250473 | 7/1959 | Spain . | |

OTHER PUBLICATIONS

Kauffmann et al., Chem. Abs. vol. 65 entry #7138f (1966).
Ishikawa et al., Chem. Abs. vol. 73, entry 66451m (1970).
Chem. Abstracts, vol. 61, pp. 3067-3069, Masatomo Hamana and Kuzuhisa Funakoshi.
CA, 55, 18128C (Refers to Spanish Patent No. 250,473), Improvement of Bleaching Properties etc., Molinsy Poigarnau, et al. (1961).
CA, 47, 5704(i), Charles Wheelock (1953).

Primary Examiner—Mukund J. Shah
Assistant Examiner—Andrew G. Rozncki
Attorney, Agent, or Firm—Donald Brown

[57] ABSTRACT

The present invention is concerned with the compound of formula (I)

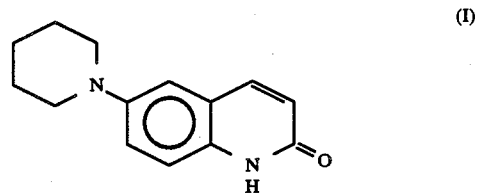

and its acid addition salts.

The invention is also directed to the use of the compound of formula (I) and its pharmaceutically acceptable acid addition salts as positive conotropic agents in mammals.

5 Claims, No Drawings

6-PIPERIDYL CARBOSTYRIL COMPOUNDS AND COMPOSITIONS CONTAINING THEM

The present invention relates to a novel quinoline derivative and its use in medicine as an inotropic agent especially for use in the treatment of congestive heart failure. Congestive heart failure is defined as the condition whereby the heart is incapable of supplying an adequate volume of blood to organs commensurate with their needs. This disorder can be caused by a primary deficiency in cardiac muscle (deteriorating myocardial contractility) or as a secondary response to hypertension or various cardiomyopathies. The depressed contractile function leads to a reduced ejection fraction (incomplete emptying of the ventricles after systole) with resulting increased myocardial wall stretch and further reduction in contractility. A useful cardiotonic drug should have positive inotropic property (the ability to increase the force and rate of myocardial contractions) to improve ejection fraction and also vasodilatory properties to further facilitate cardiac emptying.

According to the present invention, there is provided the novel compound of formula (I)

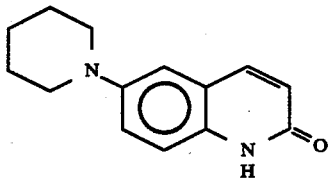

6-piperidinocarbostyril also known as 6-piperidino-2(1H)-quinolinone, hereinafter referred to as "compound (I)", and its acid addition salts. The compounds according to the invention have been found to possess and advantageous positive inotropic effect which renders such compounds useful for the treatment of, for example, congestive heart failure or heart failure associated with cardiomyopathy, myocardial infarction or cardiogenic shock while avoiding or obviating problems associated with the use of cardiac glycosides and sympathomimetics. The above compounds according to the invention have also been found to have a vasodilatory effect which is of additional benefit in the treatment of congestive heart failure.

The present invention also includes the acid addition salts of compound (I). These salts may be formed by protonation of the basic nitrogen. While it will be appreciated that acid addition salts of compound (I) may be formed with a large number of organic and inorganic acids, for therapeutic use only pharmaceutically acceptable acid addition salts are appropriate. Such pharmaceutically acceptable salts include but are not limited to those derived from hydrochloric, hydrobromic, phosphoric, malic, maleic, fumaric, citric, sulfuric, lactic or tartaric acid. The hydrochloride salt is particularly preferred. However, the present invention also includes other acid addition salts which may be used for isolating, purifying or characterizing compound (I).

The present invention also includes:

(a) a method for the treatment of clinical conditions wherein a positive inotropic agent is indicated in a mammal in need thereof which comprises administering to the mammal, e.g., a human, an effective treatment amount of compound (I) or a pharmaceutically acceptable salt thereof;

(b) compound (I) or a pharmaceutically acceptable acid addition salt thereof for use in human medical therapy, for example, the treatment of clinical conditions wherein a positive inotropic agent is indicated;

(c) the use of compound (I) or a pharmaceutically acceptable salt thereof in the manufacture of a pharmaceutical formulation for the treatment of clinical conditions wherein a positive inotropic agent is indicated.

The amount of the active compound, i.e., compound (I), or a pharmaceutically acceptable salt thereof, required to produce the desired level of inotropic effects in mammals, including humans, will, of course, vary with the route of administration and the condition of the mammal undergoing treatment and is ultimately at the discretion of the physician or veterinarian. However, a suitable oral dose of compound (I) for a mammal, e.g., human, is in the range of from 0.01 to 100 mg per kilogram of body weight per day: preferably in the range of 0.05 to 20 mg/kg body weight per day and most preferably in the range of 0.5 to 20 mg/kg body weight per day. The desired dose is preferably presented as two to four subdoses administered at appropriate intervals throughout the day. Thus, where four subdoses are employed each will lie preferably in the range of from 0.0125 to 5.0 mg/kg p.o. The corresponding doses of physiologically acceptable salts of compound (I) will be adjusted accordingly to provide the appropriate amounts of compound (I).

Compound (I) can be given as an intravenous sterile bolus injection from once to about four times per day. A suitable dose for a mammal is in the range of 0.001 to 100 mg/kg body weight, preferably in the range of 0.01 to 0.25 mg/kg body weight per injection. Compound (I) can also be administered as an intravenous infusion at doses that maintain the desired increase in cardiac performance.

While it is possible for compound (I) or a pharmaceutically acceptable acid addition salt thereof to be administered alone as the raw chemical, it is preferable to present it in a pharmaceutical formulation. Formulations of the present invention, both veterinary and for human medical use, comprise compound (I) or a pharmaceutically acceptable salt thereof (hereinafter collectively referred to as the active compound) together with one or more pharmaceutically acceptable carrier(s) thereof and optionally other therapeutic ingredients. The carrier(s) must be pharmaceutically acceptable in the sense of being compatible with the other ingredients of the formulation and not deleterious to the recipient thereof. The other therapeutic ingredient(s) may include other inotropic agents or vasodilating agents. Accessory ingredients such as preservative, coloring, sweetening, flavoring, etc. agents may also be added to enhance the appearance, taste or storage life of the formulation.

The formulations include those suitable for oral, rectal, topical or parenteral (including subcutaneous, intramuscular and intravenous) administration. They may conveniently be presented in unit dosage form and may be prepared by any of the methods well known in the art of pharmacy. All methods include the step of bringing the active compound into association with a carrier and accessory ingredients. In general, the formulations are prepared by uniformly and intimately bringing the active compound into association with a liquid carrier or a finely divided solid carrier or both and then, if necessary, shaping the product into the desired formulation.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquids such as a syrup, an elixir, an emulsion or a draught. The active compound may also be presented as bolus, electuary or paste. Tablets or capsules may be prepared as sustained release formulations if desired.

A tablet may be made by compression or moulding, optionally with one or more accessory ingredients. Compressed tablets may be prepared by compressing in a suitable machine from a free flowing form (such as a powder or granules) of the active compound optionally mixed with a binder lubricant, dispersing agent or other agent(s) to enhance appearance or promote stability. Moulded tablets may be made by moulding in a suitable machine from mixture of ingredients similar to those used in producing compressed tablets.

A syrup may be made by adding the active compound to a concentrated, aqueous solution of sugar, for example sucrose, to which may also be added any accessory ingredient. Such accessory ingredient(s) may include flavorings, agent(s) to retard crystallization and agent(s) to increase the solubility of the other ingredients.

Formulations suitable for parenteral administration conveniently comprise a sterile aqueous preparation of the active compound which is preferably isotonic with the blood of the recipient. Formulations for rectal administration may be presented as a suppository with a usual carrier such as cocoa butter.

The present invention further includes a process for the preparation of compound (I) and pharmaceutically acceptable acid addition salts thereof which comprises reacting 6-aminocarbostyril with a compound of formula L-$(CH_2)_5$-L', wherein L and L', which may be the same or different, are suitable leaving groups such as bromo, in the presence of a base such as anhydrous sodium carbonate, and optionally converting the resulting compound (I) into a pharmaceutically acceptable salt thereof. The reaction of the 6-aminocarbostyril and 1,5-pentamethylene compound is typically carried out in an aprotic solvent, such as dimethylformamide, at a temperature of from 75° to 80° C. The compound (I) may be converted into a physiologically acceptable salt thereof in conventional manner, for example, by treatment with the appropriate acid, for example, using an alcoholic solution thereof.

The following examples are provided to illustrate the present invention and should in no way be construed as a limitation thereof.

EXAMPLE 1

6-Piperidinocarbostyril a. 6.Nitrocarbostyril

Nitric acid (70%), 2.3 mL, was added dropwise to a stirred mixture of 2-hydroxyquinoline (available commercially or by one of the methods described in Beilstein 21, 77) 3.5 g (0.024 mole), in 20 mL of concentrated sulfuric acid at 0° C. The reaction mixture was stirred for 2 hours at room temperature and then poured into ice and water. The resulting solid was collected by filtration, washed with cold water and then digested twice with hot methanol to yield 3 g (67%) of 6-nitrocarbostyril as crystals; m.p. 280°–282° C.

Anal. Calcd. for $C_9H_6N_2O_3$: C, 56.84; H, 3.18; N, 14.74.

Found: C, 56.81; H, 3.18; N, 14.72.

b. 6-Aminocarbostyril

In a Parr catalytic hydrogenation apparatus 6-nitrocarbostyril, 5.3 g (0.028 mole), in 150 mL of methanol and 0.5 g $PtO_2$ were shaken in a hydrogen atmosphere. The resulting yellow solid was extracted with refluxing methanol to yield 6-aminocarbostyril, 3.5 g, as yellow crystals; m.p. 315°–317° C.

Anal. Calcd. for $C_9H_8N_2O$: C, 67.48; H, 5.03; N, 17.49

Found: C, 67.28; H, 4.98; N, 17.38.

c. 6-Piperidinocarbostyril

A mixture of 6-aminocarbostyril, 3.2 g (0.02 mole), 1,5-pentamethylene dibromide, 4.6 g (0.02 mole), sodium carbonate (anhydrous), 2.8 g (0.028 mole) and dimethylformamide, 30 mL was heated for 3 hours at 75°–80° C. in a water bath with occasional swirling. At the end of the reaction period the mixture was diluted with water, 250–300 mL, with stirring and cooling. The precipitated insoluble solid was collected by suction filtration and was washed repeatedly with cold water. The resulting product was crystallized twice from hot ethyl acetate and gave 2.05 g (45%) of 6-piperidinocarbostyril; m.p. 225°–226° C.

Anal. Calcd. for $C_{14}H_{16}N_2O$: C, 73.66; H, 7.06; N, 12.27

Found: C, 73.60; H, 7.07; N, 12.26.

EXAMPLE 2

6-Piperidinocarbostyril Hydrochloride

6-Piperidinocarbostyril, 0.5 g (0.002 mole), was suspended in 15 mL methanol. Five mL ethanolic hydrogen chloride was added, and the mixture was digested in a steam bath for 15 minutes until part of the methanol was evaporated After cooling, filtration and washing with ethyl acetate, the resulting white crystals, 0.4 g, were recrystallized by dissolving in warm methanol and adding ethyl acetate. The yield was 0.4 g 6-piperidinocarbostyril hydrochloride; m.p. 298°–300° C.

Anal. Calcd. for $C_{14}H_{16}N_2O \cdot HCl$: C, 63.51; H, 6.47; N, 10.58; Cl, 13.39

Found: C, 63.60; H, 6.53; N, 10.56; Cl, 13.45

EXAMPLE 3

In Vitro Inotropic Activity

Cat papillary muscles were dissected out of the ventricular cavity and clamped against a punctate electrode. The tissues were stimulated through the punctate electrode and an external platinum electrode with threshold voltage +30% with square waves of 5 msec duration at a frequency of 0.5 Hz. Tissues were put under resting tensions of 1.0 g. Changes in force were detected via a Grass FT 0.03 isometric transducer and recorded as grams tension on a Beckman dynograph recorder. Tissues were incubated in KrebsHenseleit solution and all assays were carried out at 34° C.

Aqueous solutions having different concentrations of the compound of Example 1 were added to the organ batch in a cumulative manner at 1.0 log unit intervals and left in the bath for at least five minutes. If a response was detected, then the tissues were left to attain a steady state. Responses were expressed as a fraction of the maximal response to isoproterenol. Decreases were expressed as % of the basal stimulated-inotropic force. All tissues were incubated with 0.3 $\mu$M propanolol and 1 $\mu$M phentolamine to eliminate possible effects of released catecholamines.

The inotropic Activity Index (IAI) is a number reflecting the inotropic activity of a compound on cat papillary muscles and is calculated as the product of the maximal response of the tissue to the compound (as a fraction of the maximal response to isoproterenol, the standard drug) and the $pD_2$ (-log of the molar concentration of the compound which produces half the maximal response). An index of $\geq 3.0$ indicates significant inotropic activity. The IAI for compound (I) wa found to be 3.3.

EXAMPLE 4

In Vivo Inotropic Activity

Four female beagle dogs, weighing 11-12.9 kg, were used in the conscious state.

Two dogs had previously been prepared with 'carotid loops' to allow measurement of arterial blood pressure by acute percutaneous catheterization. The other 2 dogs were surgically-instrumented, 2-3 weeks prior to the study, with a cannula in the descending aorta and a left ventricular pressure transducer (Konigsberg P7).

Initial experiments in the carotid loop dogs studied the effects of intravenous administration of the compound of the invention at 0.2-1.0 mg/kg on carotid arterial blood pressure, arterial dP/dt and heart rate. Subsequent studies in the instrumented dogs evaluated the effect of the compound when given intravenously (0.2-1.0 mg/kg) and orally (0.5-2 mg/kg) on aortic blood pressure, left ventricular pressure (LVP), LVdP/dt and heart rate.

Animals were supported in slings within the laboratory whilst recording the cardiovascular variables. Following stabilization and standardization with isoprenaline, 0.01-1.0 $\mu$g/kg i.v., only a single dose of the test compound was administered per test occasion with at least one day recovery between occasions. The test vehicle was also administered alone as a control. Intravenous administration was by a 1 ml/min infusion into a cephalic vein for 15 min. Stated doses of the compound are the total doses given in the 15 min infusion. Oral administration was by gavage in 1 ml/kg dose volume and washed in with 10 ml 5% dextrose. Animals were fasted overnight prior to oral administration.

The compound of Example 1 was weighed out as required on each occasion and dissolved in a minimum of 0.1 M NaOH; pH was adjusted to 5.2–5.5 with 0.1 M HCl and made to volume with distilled water. Dilutions were made in 5% dextrose.

a. Carotid loop dogs (n=2)

Intravenous infusions of the test compound at 0.2-1.0 mg/kg increased arterial dP/dt in a dose-related manner. Maximum increases of approximately 35-100%, depending on the dose, were apparent by 30-60 min following termination of the infusion. The effect persisted with little recovery to beyond 3 hours. Associated blood pressure was little changed whilst heart rate tended to increase but this was neither consistent nor dose-related.

b. Instrumented dogs (n=2)

In these animals myocardial contractility, as indicated by LVdP/dt, was again increased in a dose-related manner following intravenous infusion of the test compound of 0.2-1.0 mg/kg. Maximum effects (increases of 45-90%) were similar to that seen on arterial dP/dt. Systolic blood pressure tended to rise in association with the increased dP/dt (0.2-1.0 mg/kg) whilst diastolic pressure was slightly depressed (<10 mmHg) following 1 mg/kg. Associated heart rate was not consistently changed but tended to fall with 0.5 mg/kg and to rise with 1 mg/kg.

Oral administration of the test compound at 0.5-2 mg/kg to the same animals on separate occasions, resulted in marked increases in LVdP/dt. The effect was poorly related to dose e.g. +70-80% with 0.5-2 mg/kg. Generally maximum effects were seen by 60-120 min after dosing and persisted with little recovery to >4 hours after dosing. Additional observations following the 0.5 mg/kg dose level showed that LVdP/dt was still increased (approx. +20%) at 10 hours but had subsided by 24 hours after dosing. Associated systolic pressure tended to increase following 0.5 and 1.0 mg/kg whilst diastolic pressures were slightly reduced following 1.0 and 2 mg/kg p.o. Heart rate appeared slightly increased following 0.5 mg/kg but was little affected after the higher doses.

The compound of the invention was well tolerated and demonstrated a potent and persistent positive inotropic activity with minimal effects on arterial blood pressure and heart rate. The effect following oral administration demonstrated good oral bioavailability.

EXAMPLE 5

Pharmaceutical Formulations

| a. Tablets | |
| --- | --- |
| 6-Piperidinocarbostyril | 50 mg |
| Starch | 132 mg |
| Magnesium stearate | 18 mg |
| Lactose | 45 mg |
| Total | 245 mg |

Tablets each having the above composition are prepared in a conventional manner.

| b. Ampoules | |
| --- | --- |
| 6-Piperidinocarbostyril hydrochloride | 500 mg |
| Sodium chloride | 0.9 mg |
| Distilled water for injection | q.s. to 100 mL |

The above sodium chloride is dissolved in distilled water with warming while stirring. The resulting solution is cooled to 40° C., and the compound of the invention is dissolved therein. Then distilled water for injection is added to the final volume. The mixture is filtered using a suitable filter paper to sterilize and then filled in an ampoule of 1 mL, thus forming the preparation for injection.

I claim:

1. The compound of formula (I)

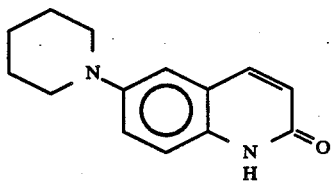

(I)

2. A pharmaceutically acceptable acid addition salt of 6-piperidinocarbostyril.
3. The hydrochloride salt of 6-piperidinocarbostyril.
4. A pharmaceutical composition comprising 6-piperidinocarbostyril or a pharmaceutically acceptable acid addition salt thereof together with a pharmaceutically acceptable carrier therefor.
5. The composition in accordance with claim 4 in the form of a tablet or capsule.

* * * * *